United States Patent [19]

Moreno et al.

[11] Patent Number: 5,543,562
[45] Date of Patent: Aug. 6, 1996

[54] NON-HYGROSCOPIC MONOAMMONIUM SALTS OF PHOSPHONIC ACIDS OR PHOSPHINIC ACIDS

[75] Inventors: Fulgencio Powell Moreno; Laszlo Litkei; Vilmos Galamb; Imre Gulyas; Janos Repasi; Agota Repasine Veres; Jozsef Vigh; Istvanne Koczka; Edit Fehervari; Laszlone Roka; Laszlone Pethe; Jozsef Neu, all of Tiszavasvari, Hungary

[73] Assignee: Monsanto Europe S.A./N.V., Brussels, Belgium

[21] Appl. No.: 422,265

[22] Filed: Apr. 14, 1995

Related U.S. Application Data

[62] Division of Ser. No. 192,414, Feb. 4, 1994, Pat. No. 5,410, 075, which is a division of Ser. No. 869,925, Apr. 16, 1992, Pat. No. 5,324,708.

[30] Foreign Application Priority Data

| Apr. 16, 1991 | [HU] | Hungary | 12 48/91 |
| Jul. 19, 1991 | [HU] | Hungary | 24 27/91 |
| Dec. 27, 1991 | [HU] | Hungary | 41 15/91 |

[51] Int. Cl.$^6$ .................. C07F 9/38; C07F 9/30; A01N 57/02; A01N 57/12
[52] U.S. Cl. .................. 562/17; 562/8; 562/16; 504/127; 504/206
[58] Field of Search .................. 504/206, 127; 562/8, 16, 17

[56] References Cited

U.S. PATENT DOCUMENTS

| 3,799,758 | 3/1974 | Franz | 504/206 |
| 3,837,834 | 9/1974 | Hill et al. | 504/207 X |
| 3,929,450 | 12/1975 | Hamm et al. | 562/17 |
| 4,033,896 | 7/1977 | Mitchell et al. | 252/389 A |
| 4,341,549 | 7/1982 | Large et al. | 562/17 X |
| 4,376,644 | 3/1983 | Large | 562/17 X |
| 4,431,594 | 2/1984 | Broadhurst | 562/17 |
| 4,437,874 | 3/1984 | Large | 562/17 X |
| 4,464,194 | 8/1984 | Prisbylla | 562/17 X |
| 4,475,942 | 10/1984 | Bakel | 562/17 X |
| 4,486,356 | 12/1984 | Bakel | 562/17 |
| 4,507,250 | 3/1985 | Bakel | 562/17 |
| 4,525,202 | 6/1985 | Large et al. | 562/017 X |
| 4,931,080 | 6/1990 | Chan | 504/207 |
| 5,047,079 | 9/1991 | Djafar et al. | 504/206 |

FOREIGN PATENT DOCUMENTS

| 0124351 | 11/1984 | European Pat. Off. | 562/17 |
| 2363634 | 6/1974 | Germany | 562/17 |
| 58-03608 | 10/1983 | WIPO | 562/17 |

*Primary Examiner*—Floyd D. Higel
*Attorney, Agent, or Firm*—Herbert Dubno; Jonathan Myers

[57] ABSTRACT

A solid, non-hygroscopic salt of the Formula (I)

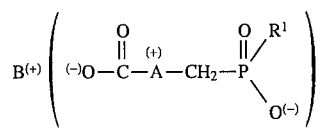

wherein $R^1$ is hydroxy or alkyl;

A is $C_1$ to $C_4$ alkyl-amino or an amino-alkyl group containing a primary or a secondary amino group; and B is ammonium ion or an alkyl-substituted ammonium ion, which is substantially free of a diammonium salt

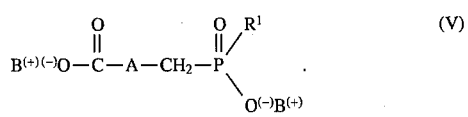

5 Claims, 6 Drawing Sheets

NON-HYGROSCOPIC MONOAMMONIUM SALTS OF PHOSPHONIC ACIDS OR PHOSPHINIC ACIDS

This is a divisional of application Ser. No. 08/192,417, filed on 04 Feb. 1994, now U.S. Pat. No. 5,410,675 which is a divisional of Ser. No. 07/869,925 filed on 16 Apr. 1992, now U.S. Pat. No. 5,324,708.

FIELD OF THE INVENTION

The invention relates to new mono-ammonium salts, their preparation and use as active ingredients of pesticides.

More particularly the invention relates to new solid, non-hygroscopic mono-ammonium salts of the formula I

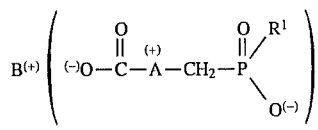

which are substantially free of diammonium-salts of the formula V,

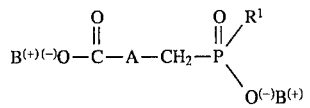

processes for their preparation, pesticide compositions containing the same, as well as preparation and use of said pesticide compositions.

In this specification the meaning of the substituents in the formulae is always the following:

—$R^1$ stands for hydroxy or alkyl-groups,
—A stands for 1–4 alkyl-amino- or amino-alkyl-groups containing primary or secondary amino-groups, preferably —$CH_2$—NH— or $CH(NH_2)$—CH-groups,
—B stands for ammonium-ion, or alkyl-substituted ammonium-ion,
—$R^2$ stands for hydrogen, hydroxyl-, optionally substituted 1–4 alkyl-groups, optionally substituted aryl-group.

BACKGROUND OF THE INVENTION

The salts of formula I are known as active ingredients of pesticides and their preparation and properties have been described in the literature. The mono-ammonium salts of formula I, however, are never described as appearing in a form other than as hygroscopic products, which are not resistant against the humidity of the normal atmosphere so that their application as pesticides was therefore only brought about by dissolving the products in water and selling the product in aqueous solutions.

The inconvenience of this procedure is clear. It was therefore the aim of our invention to find a method whereby the mon-ammonium salts of formula I—especially the mono-isopropylammonium salt of N-(phosphonomethyl)-glycine and the mono-isopropylammonium salt of (3-amino-3-carboxypropyl)-methane phosphinic acid can be obtained in a form which is non-hygroscopic, enabling thus the transportation, commercialization and even the use in solid form, or—when direct use of the pesticide on the field is carried out in aqueous solution—to ensure that the solid can be dissolved before use, bringing thus transportation and storage to reasonable costs as compared with the present situation when aqueous solutions are transported and stored. The aqueous solutions in commerce contain 30–50% of the active ingredient as a maximum. Handling of the hygroscopic salts also causes environmental and health-care problems which would be avoided with non-sticky, non-hygroscopic products. The products have mostly acidic character and attack even the material in which they are transported so that greatest care and the proper material for their protection is needed—which all increase the costs of application.

The most important representatives of the compounds of formula I are the pesticide ingredients mono-isopropylammonium salt of N-(phosphonomethyl)-glycine and the mono-isopropylammonium salt of (3-amino-3-carboxypropyl)-methane phosphinic acid—however their ammonium-salts are also important.

The above salts, their preparation and use are described in several publications such as U.S. Pat. Nos. 3,315,675, 3,56, 672, 4,405,531, 3,868,407, 4,140,513, 4,315,765, 4,397,676 and HU-Patent 184,601 as well as U.S. Pat. Nos. 3,288,846, 4,507,250, 4,147,719, 4,487,724, German Patent 3,312,165, European Patents 249,188, 265,412, 301,391, and Japanese Patents 60/248,190, 02/190,196, 59/181,288.

Different methods were developed to avoid the consequences mentioned above. Thus different additives were proposed as auxiliary agents to ensure the production of wettable powders and their use e.g. European Patents 256, 942, 352,508, Japanese Patents 01,42,409, 58,18,311, 62/175,407, 62/175,408, and U.S. Pat. No. 4,405,531. However when used in practice, great care has to be taken to protect these powders against humidity, to use up the bags when opened, to store the products under proper conditions etc.—otherwise the additional materials do not give the results that are desired when used over a long time period. Another approach to the problem was the suggestion to spray-dry the product (Jap. Pat. 63 10. 701) or again a different one to admix the salt with a solvent and a moulded surface active agent—giving thus a mixture from which the solvent is evaporated and the surface active agent is cooled until solidified, whereupon the solid product is formulated (European Patent 02,06,537).

The preparation of the salts is mostly brought about by reacting the acidic partner with the basic partner reactant in aqueous media, (e.g. Hungarian Patent 185,003, Swiss Patent 620,812 and German Patent 2,717,440) though the literature also teaches reaction of the acid with the basic reactant without solvents, whereupon the mould of surface active agent is added to the reaction mixture and formulation is carried out after cooling of the mixture. (See also Spanish Patent 530,743 where benzene or water are proposed as solvents for a similar method.)

All publications are common—when making any statement about the quality of the products obtained—that they are hygroscopic e.g. German Patent No.2,717,440; Swiss Patent No.620,812 for the ammonium salt of glufosinate, and some state that the products are solidified as glassy materials which can be ground in mortars but still are hygroscopic when stored.

According to Hung. Pat. Appl. 1322/90 a new formulation of N-(phosphonomethyl)-glycine is disclosed consisting of a water-soluble bag containing the sodium or the potassium salt of N-(phosphonomethyl)-glycine as a wettable powder, which is easy to use. The authors of said patent teach, that they were unable to make similar formulations using the mono-isopropylammonium salt of N-(phosphonomethyl)-glycine because of the extreme hygroscopic nature of the mono-isopropylammonium salt. Nor is the aqueous solution of the mono-isopropylammonium salt of N-(phosphonomethyl)-glycine suitable (according to said publication)

because the solution dissolves the material of the bag before use.

When investigating some of the products obtained according to some of the known methods e.g. when reproducing the processes of European patent 02/56,608 and Spanish Patent 530,743 we found that these mono-isopropylammonium salts always contained certain amounts of di-ammonium-salts of formula V together with acids of formula II

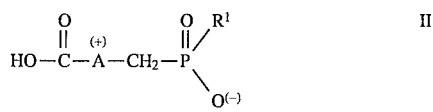

The presence of small amounts of the di-ammonium-salts of the formula V is not evident from the analysis data of the products obtained by way of classical analysis methods: the content of free acids of formula II together with the content of di-ammonium-salts of formula V might give analytical data as a total result which hide the presence of the di-ammonium salts in the products.

When isolating di-ammonium-salts of formula V we ascertained that these salts differ considerably from the mono-ammonium salts as regards hygroscopicity so that slight amounts of the di-ammonium-salts influence the hygroscopic properties of such salts dramatically.

When investigating the N-(phosphonomethyl)-glycine obtained with known methods by means of FT-IR spectroscopy we found that the products always contained the carbonyl valency oscillation bonds of free N-(phosphonomethyl)-glycine at 1717 and 1733 cm$^{-1}$ wave length and the carboxylate oscillations of the free carboxylate in the N-phosphonomethyl)-glycine di-isopropyl-ammonium-salt at 1561 and 1633 cm$^{-1}$. The change of the proportions of these bonds shows the change in the ratio of components. This was shown by preparing standard samples of the mono- and the di-iso-propyl-ammonium salts and taking their calibration spectra.

It can be seen from the IR spectroscopic data that also glufosinate exists in two different forms of twin-ionic structure. Thus the carboxyl group can appear both in dissociated form at 1640 and 1600 cm$^{-1}$ and in non-dissociated form at the absorption band at 1733 cm$^{-1}$ and 1728.

Care has to be taken when preparing the samples as well, Sometimes the mono-ammonium-salts—which are contaminated with di-ammonium-salts as well as with the free acid—are subject to additional reaction steps when the samples are dissolved before taking the spectra—giving thus results that are not typical for the product before measurement.

When comparing the spectra obtained with our own methods it is clear that in the products prepared according to our invention the un-dissociated carboxyl group absorption bonds disappear at 1730 cm$^{-1}$ and the dissociated carboxyl bonds which are characteristic for the salts increase at 1640 and 1600 cm$^{-1}$.

If one already has the above spectroscopic data the HPLC methods and automatic melting point analytical methods can then be used to complete the definition of the properties of the new salts.

"Non-hygroscopic" according to our invention means, that when exposed at 25° C. to an environment containing 60% humidity no observable uptake of water takes place within 3 weeks or this uptake is less than 0.1%. The salts are crystalline, they have melting point ranges that are different from those published before and their water-solubility is somewhat increased as compared with the salts prepared with the known methods.

OBJECTS OF THE INVENTION

The object of the invention is to obtain non-hygroscopic salts of formula I.

Preferred products according to our invention are the solid, non-hygroscopic mono-isopropylammonium salts of N-(phosphonomethyl)-glycine of the α and/or β crystal type.

The α-crystal-type has a melting range of 158°–163° C. and the characteristic values of crystal-lattice-levels when measured by way of X-ray-diffraction are as follows: 11.0, 9.06, 5.94, 5.54, 4.13, 3,71, while the characteristic absorption bands obtained by FT-IR-spectroscopy are 1660, 1600, 1553, 1545, 1075, 513 and 475 cm$^{-1}$.

Other preferred products according to our invention are the solid, non-hygroscopic, crystalline mono-isopropylammonium salts of N-(phosphonomethyl)-glycine of the β crystal type, having a melting range of 143°–154° C. and the characteristic values of crystal-lattice-planes when measured by way of X-ray-diffraction are as follows: 7.00, 4.47, 3.35, 2.815, while the characteristic absorption bands obtained by FT-IR-spectroscopy are 1645, 1594, 1561, 1541, 1066, 500 and 455 cm$^{-1}$.

The mono-isopropylammonium salt of N-(phosphonomethyl)-glycine can thus appear in two different crystal types which we named α and β types. None of these has ever been described as a non-hygroscopic, crystalline product.

A further preferred product according to our invention is the solid, non-hygroscopic, crystalline (3-amino-3-carboxypropyl)-methane-phosphinic acid mono-isopropylammonium salt having a melting point range of 199°–203° C., while the characteristic absorption bands obtained by FT-IR-spectroscopy are 1640, 1601, 1530, 1138, 1037, 750 and 471 cm$^{-1}$.

A further subject of our invention is the process for the synthesizing of a solid, non-hygroscopic salt by preparing the mono-ammonium-salt of formula (I) according to a method known generally for the preparation of salts, whereby—along with avoiding other contaminations—on the course after salt-formation of the di-ammonium-salt of the formula (V) is eliminated or its formation is repressed.

SUMMARY OF THE INVENTION

Preferred processes according to our invention comprise the use of the following processes alone or in combination with each other.

a.)

reacting the acid of the general formula (II) with a reactant of basic (alkaline) character capable to form the ion B$^+$ —in an organic, polar solvent or in a solvent-mixture containing an organic, polar solvent, in which the salt and acid of formulae (I) and (II) are not, or only slightly soluble, while the reactant of basic character and the di-ammonium-salt of formula (V) formed as a byproduct are readily soluble, and optionally the reaction mixture is heated subsequently or b.)

a di-ammonium-salt of the formula (V), is reacted with an acid of the formula (II) under the reaction conditions of the method a) or c.)

an acid of the formula (II) is reacted with a salt capable to form the ion B$^+$ under the reaction conditions of the method a) or d.)

a hygroscopic salt of the (I) is extracted with an organic, preferably polar solvent or a solvent-mixture containing an organic, polar solvent, in which the mono-ammonium salt of formula (I) is insoluble or slightly soluble, while the di-ammonium-salt of formula (V) is readily soluble or e.)

eliminating at room temperature in vacuo or with heating from a di-ammonium salt of formula (V) or from a mono-ammonium salt which is contaminated with such di-ammonium-salt the quantity of the amine containing the $B^+$-ion which is above the mole-equivalent, or f.)

reacting a salt of the acid of the formula (II), using the reaction conditions of the a.) method with a reactant which is capable to form the ion $B^+$—and optionally isolating the salt of formula (I) thus formed preferably by filtration.

When carrying out the above processes it is preferable to use as a starting acid N-(phosphonomethyl)-glycine of formula (III)

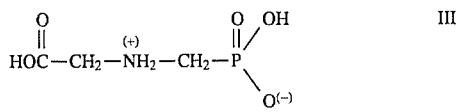

or (3-amino-3-carboxy-propyl)-methane-phosphinic acid of the formula (IV)

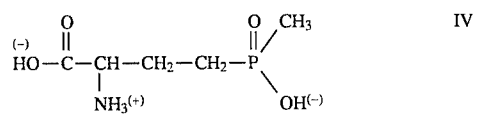

Solvents that are suitable for our process are aliphatic alcohols containing 1–6 carbon atoms and/or poly-alcohols and/or aromatic alcohols containing 1–6 carbon atoms in the alkyl side chains. It is preferable to prepare N-(phosphonomethyl)-glycine-mono-isopropyl-ammonium-salt or—mono-ammonium-salt in the presence of ethanol and/or propanol. Preferred temperature ranges for the method c.) reactions are 0°–150° C., preferably 20°–80° C.

According to method a.) it is essential to use the proper solvents that have to be chosen according to our invention. As stated above, it is the solubility tests that have to be performed before such a choice is made. It is essential that such solvents have to be used in which the salt of formula (I) and the acid of formula (II) are practically insoluble or but slightly soluble, while the reactant of alkaline character and the di-ammonium-salts of formula (V) are readily soluble.

A supposition of how the process might take its course is the following: The reaction starts on the surface of the acid particles suspended in the solvent system. Since the acid is dibasic and the amines are present in excess, on the surface of the acid the di-ammonium salts are formed, which because they are readily soluble in the solvent—leave the surface of the acid particles and dissolve, leaving the surface open to enter into reaction with further amounts of amine. As soon as the amine or other basic reactant is used up, the remaining dispersed acid and the di-ammonium-salt in solution can enter into an ion-transfer reaction so that the mono-ammonium salt is formed. Since the solubility of the mono-ammonium-salt is very small in the solvent-mixture used, the mono-ammonium salt precipitates continuously.

We have found that polar organic solvents or such solvent mixtures which contain organic polar solvents are suitable for the purpose of method a.) of our invention.

The above theory is supported by the changes which can be observed when e.g. N-(phosphonomethyl)-glycine is reacted with isopropylamine according to method a.) of our invention:

When a dispersion of the N-(phosphonomethyl)-glycine in absolute ethanol is made a liquid of strong white color is obtained. On subsequent addition of isopropylamine the colour become lighter and—on addition of the whole quantity of isopropyl amine and eventually after heating—the reaction mixture gets clear, almost transparent, followed by precipitation of the mono-ammonium-salt on cooling.

Once knowing that the above method is suitable for the preparation of the mono-ammonium-salt which is substantially free of the di-ammonium salt, the application of other methods is also possible.

To investigate the process we prepared the di-ammonium-salt using double amounts of the isopropylamine and made tests concerning this product and its solubility. /see Tables IV and V. We then used this products as starting materials for methods b.) and e.) of our process.

The above experiments also show why it was not possible to obtain pure mono-ammonium-salts according to the methods of EP 256 608 and Spanish Patent 530 743: They used solvents in which the di-isopropylammonium salt is not readily soluble, and resulting in considerable contamination of the mono-ammonium-salt with both the di-ammonium-salt and the starting acid.

When using the method c.) it is adventageous to react the acid of formula (II) with the salt formed with a 1 or 2 basic carboxylic acid of the pK-value of the range 2.27 to 5.8. The acids may have the formula (VI)

Thus when preparing alkyl-ammonium salts according to the method c.) one may proceed by applying the alkyl-ammonium salt of the acid of the formula (VI) which is added to the reaction in solid form or in solution.

Preferred temperature ranges for the method c.) reactions are 0°–150° C., preferably 20°–80° C.

According to our method c.) the salts of the amines are used. The salts are generally easier to handle than the amines, which have rather low boiling points. Preferable carboxylic acids are for example acrylic acid, benzoic acid, acetic acid, formic acid, propionic acid, butyric acid, valeric acid and others.

The salts may be prepared separately and the isolated salts may be added to the acids of formula II. However, one may also proceed by preparing the salt in solution, and adding the solution to the acid without isolating the salt after making the proper analytical evaluations.

The processes according to our invention are simple, they do not need any special equipment, they do not raise environmental problems while leading to the new crystalline mono-ammonium salts according to our invention.

A further object of our invention are herbicidal or plant-growth-regulating compositions containing as an active ingredient an effective amount of the crystalline, non-hygroscopic salts of the general formula (I).

Especially important are those herbicidal or plant-growth-regulating compositions according to our invention which contain as an active ingredient an effective amount of a crystalline, non-hygroscopic (3-amino-3-carboxy-propyl)-methane-phosphinic acid mono-isopropyl-ammonium salt or of the mono-isopropylammonium salt of N-(phosphonomethyl)-glycine of the α and/or β crystal type.

Preferred compositions according to our invention include compositions containing as an active ingredient 0.1 to 99.9% of the above salts along with additive and auxiliary products which are used in the pesticide industry and/or products which favorably modify the properties of the composition when applied for agricultural use.

As additive and auxiliary products surface active agents reducing surface tension may be used which may be cationic, anionic, non-ionic or amphoteric as well. Further additives include adjuvants, adhesion promoting and decreasing substances, inhibitors of dust and foam formation, promoters of dissolution, solid or liquid vehicle substances, dispersing, coloring agents, products that increase resistance against rain or corrosion, activators and the like.

Preferable auxiliary products are the following:
—water-soluble alkyl-sulphates, alkyl-phosphates,
—alkyl-benzene-sulphonate,
—naphthyl-sulphonates, alkyl-naphthyl-sulphonates,
—sulphatized fatty alcohols, amines, acid amides,
—sulphatized, or sulphonated fatty acid esters,
—sulphonated plant oils,
—alkyl-phenols such as iso-octyl-phenol and nonyl-phenol
—polyoxy-ethylene derivatives and hexythal anhydrides
—poly(oxy-ethylene) derivatives of mono-(long carbon chain) fatty acid esters
—polyoxy-ethylene-alkyl-ether, polyoxy-ethylene-alkyl-aryl-ethers,
—polyoxy-ethylene-alkyl-aryl-ether formaldehyde condensates,
—polyoxy-ethylene-alkylene-aryl-ethers,
—polyoxy-alkylene-alkyl esters,
—polyoxy-alkylene-sorbital-, sorbitane and glycerol esters,
—polyoxy-alkylene block copolymers,
—polyoxy-alkylene-allyl-sulphonamides,
—polyoxy-alkylene-alkyl-glycerol-esters,
—polyoxy-alkylene-resin esters,
—polyoxy-propylene blockcopolymers,
—polyoxy-ethylene-oleyl ethers,
—polyoxy-alkylene-alkyl-phenols and mixtures thereof
—polyoxy-alkylene-alkyl-amines such as ethoxylated tallow-amine, ethoxylated oleic-amine,
—ethoxylated soy amine, ethoxylated cocoa amine, ethoxylated
—synthetic alkyl-amines, propoxylated amines and mixtures
—polyoxy-alkylene-alkyl and alkyl-aryl-ether-sulphates,
—polyoxy-alkylene styryl-phenyl-ether-sulphates,
—alkyl-naphthalene-formaldehyde condensates,
—alkyl-diphenyl-ether-sulphonates,
—poly-oxy-alkyne-alkyl-phosphates
—polyoxy-alkylene-phenyl-ether-phosphates,
—polyoxy-alkyl-phenol-phosphates,
—polycarboxylates, N-methyl-fatty acid laurides,
—amine-oxides, such as lauryl-dimethyl-amine-oxide,
—surface active salts of N-(phosphono-methyl)-glycine e.g. N-(phosphono-methyl-glycine N, N-bis (hydroxy-ethyl-co-cusamine salt
—saturated fatty alcohols,
—organic acid esters, lactic acid ethyl ester, dibutyl-phthalate, adipic acid-isopropylester,
—fatty acids, fatty acid salts, fatty acid esters,
—ethyl-oleate, ethyl-stearate, di-n-butyl-adipate,
—lauric acid-hexylester, dipropylene glycol-pelargonate,
—isopropyl-myristate, isopropyl-palmitate, isopropyl-stearate,
—oleic acid, oleylester, oleic acid-dodecyl-ester, polyglyceryl-lauric acid ester,
—capryl/capric acid esters of saturated fatty alcohols,
—glycerol-poly-vinyl-alchol derivatives,
—phospholypids, alkyl-polyglycoside derivatives
—methyl-, hydroxy-ethyl-, hydroxy-methyl and other cellulosese derivatives
—poly-vinyl derivatives,
—lignine sulphonates, polyperic alkyl-naphthalene sulphonates,
—poly-(methylene)-bis-(naphthalene sulphonate), N-methyl-N-(long chain) fatty acid laurates
—quaternary ammonium salts, alkyl-, and alkyl-aryl ammonium halogenides, e.g.10–18 carbon atom alkyl-dimethyl-, alkyl-trimethyl-, alkyl-benzyl-dimethyl-ammonium-chlorides e.g. cetyl-trimethyl-ammonium chloride,
—anionic, cationic, non-ionic, or amphoteric flour-aliphatic wetting agents,
—silicone-copolymer-based surface activants,
—tetraethoxy-silane derivatives, The compositions may preferably contain special inorganic or organic nitrogen containing products as additives, such as urea, urea-derivatives or further inorganic salts such as calcium-, sodium-, ammonium-chloride, -sulphate, -phosphate, -borate and the like.

They also may contain paraffine hydrocarbons, mineral oil fractions, natural plant oils, organic solvents.

Inert vehicle products such as diathomic earth, caoline, attapulgite, fullers earth, montmorillonite, bentonite, synthetic silicic acids, thiosulphates and other agents which are adjuvants when using the compositions.

Being solid products the compositions may take different forms depending of the requirements of use such as pellets, powders, tablets, granules using suitable apparatuses.

In addition to the above the compositions according to the invention may also include further products which have pesticide or other biological activity per se. These might be insecticides, fungicides herbicides, plant growth regulalin agents or chemical fertilizers, trace elements etc.

Preferable combination partners of this type are e.g. the following:
2,4-D=2,4-dichloro-phenoxy-acetic acid
endotal=7-oxobicyclo(2,21)heptene-2,3-dicarboxylic acid
2,4,5-T=2,4,5-trichloro-phenoxy-acetic-acid,
MCPA=4-chloro-o-tolyloxy-acetic acid,
MCPB=4-(4-chloro-o-tolyloxy)-acetic acid,
glufosinate=ammonium-(3-amino-3-carboxy-propyl)-methylphosphinate,
bialafos=dl-homoalanine-4-yl-methyl-phosphinate
etafon=2-chloro-ethane-phosphonic acid,
mekoprop=2-(2-methyl-4-chloro-phenoxy-propionic acid,
pikloram=4-amino-3,5,6-trichloro-picolic acid,
benzak=2,3,6-trichloro-benzoic acid,
dalapon=2,2-dichloro-propionic acid,
dikamba=3,6-dichloro-o-anis acid,
dichlorprop=2-(2,4-dichloro-phenoxy)-propionic acid
scepter=2-(4,5-dihydro-4-methyl-4-1-methyl-ethyl(-5-oxo-1H-imidazole-2-yl)-3-quinoline carboxylic acid
pursuit=2-[4,5-dihydro-4-methyl-4-)1-methyl-ethyl)-5-oxo-1H-imidazole-2-yl]-5-ethyl-3-pyridine carboxylic acid,
atrazin=2-chloro-4-(ethyl-amino)-6-(isopropylamino)-s-triazine
simazin=2-chloro-4,6-bis(ethyl-amino)-s-triazine,
diuran=3-(3,4-dichloro-phenyl)-1,2-dimethyl-urea,
linuron=3-(3,4-dichloro-phenyl)-1-methoxy-1-methyl-urea,
NES=1-naphthyl acetic acid,
orest=2-[3-{4,6-dimethyl-pyrimidine-2-yl}ureido-sulphonyl]benzoic acid,
glean=1-[2-chloro-phenyl-sulphonyl)-3-(4-methoxy-6-methyl-1,3,5-triazine-2-yl]-urea, allin=methyl-2-[{4-methoxy-4-methyl-1,3,5-triazine-2-yl}-amino-carbonyl]-amino-sulphonyl-benzoate, klasszik=ethyl-2-[{4-chloro-6-methoxy-pyrimidine-2-yl}-amino]-carbonyl-amino-sulphonyl-benzoate fomesafen=5-[chloro-4-{trifluoro-methyl}-phenoxy]-N-methyl-sulphonyl- 2-nitrobenzamide oxyflurofen=[2-chloro-1-{3-ethoxy-4-nitro-phenoxy}-4-(trifluoro-methyl]-benzene, —fcroe=[phenoxaprop-ethyl(+_)ethyl-2,4(-6-chloro-2-benzoxazolyl)-oxy-phenoxy]-propanoate, —alachlor=2-chloro-2',6,'-diethyl-N-(methoxy-methyl)acetanilide, —propachlor=N-isopropyl-2-chloro-acetanilide, —butachlor=N-(butoxy-methyl)-2,6-diethyl-2-chloroacetanilide, —metachlor=2-chloro-2-ethyl-6-methyl-N-(1-methyl-2-methoxyethyl)-acetanilide etc.

A further object of our invention consists in processes for the preparation of a herbicidal or plant-growth regulating compositions by formulating with the methods known for formulating of pesticides 0.1 to 99.9% of an active ingredient according to our invention together with auxiliary products used in pesticide formulation and(or with products which favorably modify the properties of the active ingredients when used including products that have biological properties or are known to be active ingredients of pesticides per se.

Further objects of our invention are herbicidal or plant-growth-regulating compositions consisting of a bag, which is solid in its dry state, which is made of a water-soluble polymer and which contains the compositions according to our invention.

Preferred products of this type are those containing the mono-isopropylammonium salt or mono-ammonium-salt of N-(phosphonomethyl)-glycine or the mono-isopropylammonium salt or mono-ammonium-salt of glufosinate.

The bags used according to the invention are of the size taking 0.1–10 kg, preferably 0.5–5 kg of the compositions according to the invention. They may preferably be totally filled with the composition of the invention. However some space might be left to facilitate addition of certain substances before use.

The bags are solid and flexible at the temperature and humidity of the ambiance. The thickness of the walls amounts to 20–100 microns, preferably to 30–60 microns and they are welded at at least one side.

The water-soluble bags used according to our invention as above are known per se. The water-soluble polymer applied may be the following:

—polyvinyl alcohol polymers, especially polyvinyl alcohol polymers plastified with polyvalent alcohols,
—methyl cellulose
—ethylene oxide copolymers
—polymers of vinyl pyrrolidone or vinyl acetate,
—gelatine, carboxy methyl cellulose, dextrose, hydroxyethyl-cellulose or
—methyl cellulose combined with poylvalent alcohols, such as ethylene glycol, propylene glycol, glycerol, sorbitol and others.

It might be necessary to protect the bags by putting them into bigger containers or collective packages. These may be made of cheap material such as plastics, cardboard or aluminium. These do not influence the safety of the products for the environment because they do not contact the pesticide within the polymer bags according to our invention directly.

The polymer bags according to our invention may contain the mono-ammonium salt of formula I alone or in form of the compositions as detailed above. They may also contain additional products such as protecting colloids, products to increase density, thiotropic products, stabilizers etc.

When using the bags according to our invention the bags are thrown into the required amount of water while stirring intensively. The polymer material disappears within about 2 minutes, the herbicide composition dissolves or disperses in the water and the liquid thus obtained can be used in the field as needed.

A further object of the invention consists in a method to kill unwanted plants or to influence the growth of plants by treating said plants in the field with an effective amount of a herbicidal or plant-growth-regulating composition according to our invention by way of dispersing the composition on the plants in the form of aqueous or water organic solvent solutions or dispersions or suspensions.

In the formulae according to this specification the symbol A also appears as symbol $A^+$ and it is understood by those skilled in the art that in these latter cases the amine forms an ammonium salt and A is in the ionized form.

The salts of formula I—as symbolized according to the present specification—represent so called "zwitterion" forming internal salts. Since not every author accepts this representation of these molecules there might be also other formulae to describe the non-hygroscopic substances according to the present invention without however effecting or limiting the subject of the invention.

Figure 1:
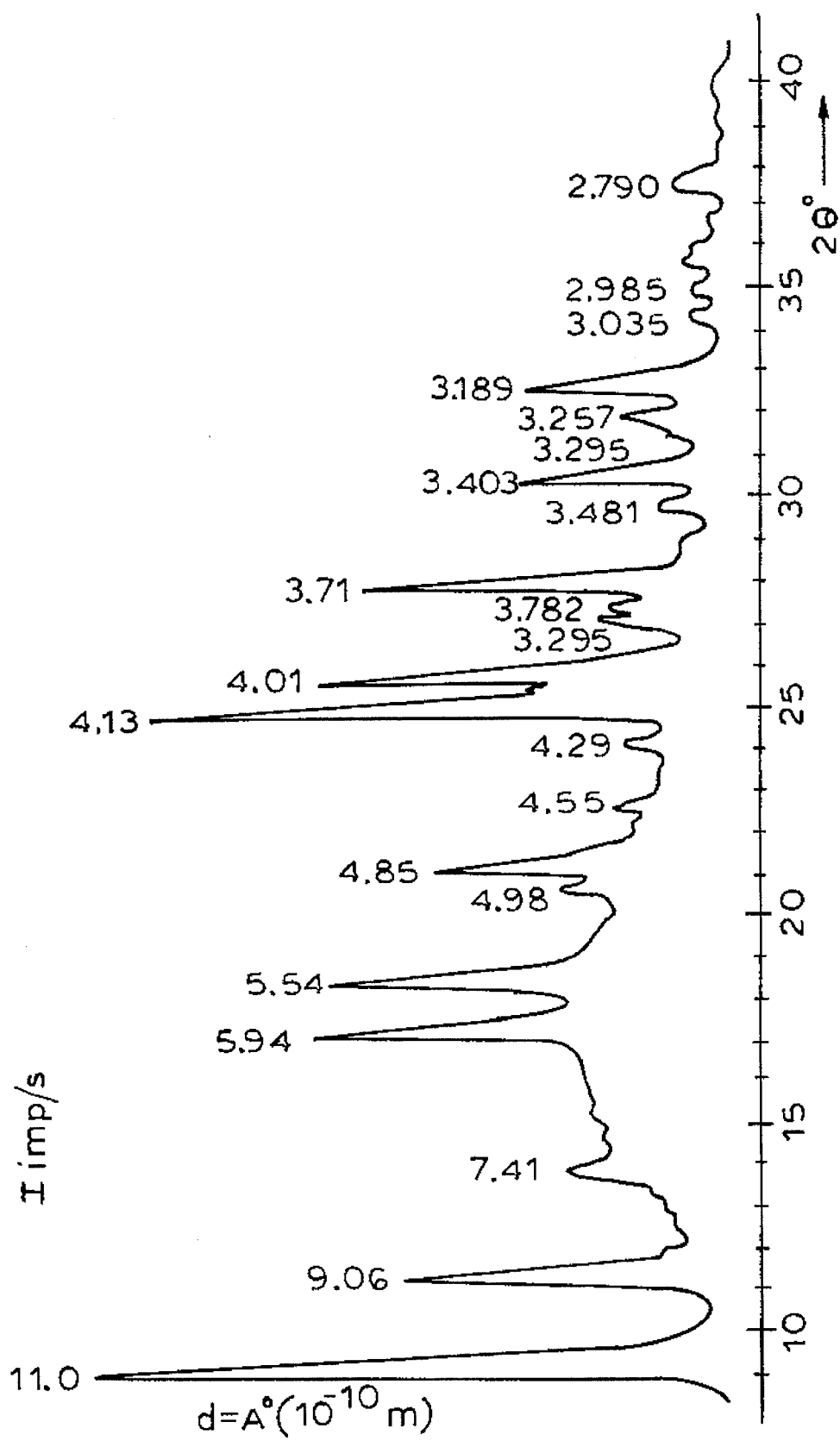
FIG. 1: X-ray diffraction spectrum of N-(phosphonomethyl)-glycine mono-isopropylammonium salt α crystal type. Intensity against angle.

Details of the invention are given in the Examples by way of illustration and not of limitation.

I. CHEMICAL EXAMPLES

Example I.1.

50 g (0.3 moles) of N-(phosphonomethyl)-glycine are reacted with 17.5 g (0.3 moles) of isopropylamine in 200 ml of 96% ethanol at room temperature. The mixture is refluxed for half an hour, filtered, concentrated by evaporation and crystallized. 69 g (0.3 moles) of crystalline, dried mono-isopropylammonium salt of N-(phosphonomethyl)-glycine are obtained. The product is not hygroscopic, readily soluble in water. Melting range 161°–163° C. It contains 73.9%

N-(phosphonomethyl)-glycine Yield 99.95%. Characteristic absorption bands (FT-IR spectroscopy, cm$^{-1}$) 1660, 1600, 1553, 1545, 1075, 513, 475, characteristic values of crystal-lattice-planes measured with X-ray diffraction: 11.0, 9.06, 5.94, 5.54, 4.13, 3.71. ($\alpha$ type crystals).

Example I.2.

100 g (0.59 moles) of N-(phosphonomethyl)-glycine are reacted with 35 g (0.59 moles) of isopropylamine in 400 ml of absolute ethanol at room temperature. The suspension warms up to 49° C. and is then refluxed for half an hour by heating to 78° C. On cooling to room temperature, filtration and drying 129.0 g (0.57 moles) of crystalline mono-isopropylammonium salt of N-(phosphonomethyl)-glycine are obtained. The product is not hygroscopic, readily soluble in water. Mp: 161°–162° C. It contains 74% N-(phosphonomethyl)-glycine. Yield: 99.86%. Characteristic absorption bands (FT-IR spectroscopy, cm$^{-1}$): 1660, 1600, 1553, 1545, 1075, 513, 475, characteristic values of crystal-lattice-planes measured with X-ray diffraction: 11.0, 9.06, 5.94, 5.54, 4.13, 3.71. ($\alpha$ type crystals)

Using the method of Example 1.2. the following results are obtained:

| Ex. | amine | solvent | pmg*-salt g/mp °C. | yield % | pmg content % |
|-----|-------|---------|--------------------|---------|----------------|
| I.3. | iso-propyl- | n-propanol | 130.7 g 159–160 | 99.9 | 74 |
| I.4. | iso-propyl | n-butanol | 129.33 g 159–160 | 99.91 | 74 |
| I.5 | iso-propyl | n-amyl-alcohol | 123.7 g 158–159 | 98.7 | 73.2 |
| I.6. | iso-propyl | dimethyl-formamide | 115.1 g 148–153? | 98 | 73.0 |

* = N-(phosphonomethyl)-glycine

Example I.7

200 g (1.18 moles) of N-(phosphonomethyl)-glycine and 140 g (2.37 moles) of isopropylamine are reacted in 600 ml of ethanol and the reaction mixture which warms up to 58° C. by reaction heat is further refluxed for half an hour. On cooling, evaporation and filtration 335.8 g (1.17 moles) of the di-(mono-isopropylamine)-salt of N-(phosphonomethyl)-glycine are obtained in the form of light crystals. The product is readily soluble in water, top. 145°–150° C. N-(phosphonomethyl)-glycine content: 57.5%.

170 g (0.59 moles) of N-(phosphonomethyl)-glycine-di-(mono-isopropylamlne)-salt are reacted with 100 g (0.59 moles) of N-(phosphonomethyl)-glycine in 400 ml of ethanol, refluxed for half an hour and the milk-like suspension is filtered on cooling to room temperature. The product obtained is dried to give 269.2 g (1.18 moles) of mono-isopropylammonium salt of N-(phosphonomethyl)-glycine, melting at 158°–160° C. The product is non-hygroscopic and contains 74% of N-(phosphonomethyl)-glycine.

Example I.8

100 kg of N-(phosphonomethyl)-glycine are added to 400 l of ethanol in an autoclave vessel of 1 m$^3$. 35 kg of isopropylamine are added under nitrogen athmosphere to the mixture of 20° C. while stirring constantly. The mixture warms up to 45° C. and is then heated to its boiling point and refluxed for 1 hour. On cooling to 20° C. the mono-isopropylammonium-salt of N-(phosphonomethyl)-glycine is centrifugated, the salt washed with 30 l of ethanol and dried after repeated centrifugation. The washing is united with the mother layer.

130.1 kg of mono-isopropylammonium salt of N-(phosphonomethyl)-glycine are obtained. Contains 74% of N-(phosphonomethyl)-glycine. The product is non-hygroscopic, readily soluble in water. Mp: 153°–156° C.

Example I.9

181 g (1 mole ) of (3-amino-3-carboxy-propyl)-methane-phosphinic acid are reacted with 59 g (1.0 mole ) of isopropylamine at room temperature in 300 ml of methanol. The mixture is refluxed at 65° C. for 30 minutes, cooled, filtered and the crystals are dried to give 232 g of mono-isopropylammonium salt of (3-amino-3-carboxy-propyl)-methane-phosphinic acid, which is non-hygroscopic, readily soluble in water, melting at 203°–203.5° C., containing 75% (3-amino-3-carboxy-propyl)-methane-phosphinic acid. Yield: 97%

Example I.10

181 g (1 mole ) of (3-amino-3-carboxy-propyl)-methane-phosphinic acid are reacted with 59 g (1.0 mole) of isopropylamine at room temperature in 800 ml of ethanol. The mixture is refluxed for 30 minutes, cooled, filtered and the crystals are dried to give 2352 g of mono-isopropylammonium salt of (3-amino-3 -carboxy-propyl)-methane-phosphinic acid, which is non-hygroscopic, readily soluble in water, melting at 199°–203° C., containing 74% (3-amino-3-carboxy-propyl) -methane-phosphinic acid. Yield: 98%.

Example I.11

181 g (1 mole) of (3-amino-3-carboxy-propyl)-methane-phosphinic acid are reacted at room temperature with 17 g (1.0 mole) of ammonia (previously dissolved at 0° C. in methanol). The mixture warms up spontaneously to 35° C. and is then refluxed at 65° C. for 30 minutes, cooled, filtered and the crystals are dried to give 193 g of (3-amino-3-carboxy-propyl)-methane-phosphinic acid ammonium salt, which is non-hygroscopic, readily soluble in water, melting at 207°–209° C., containing 90% of (3-amino-3 -carboxy-propyl)-methane-phosphinic acid. Yield: 97.5%

Example I.12

Figure 3:
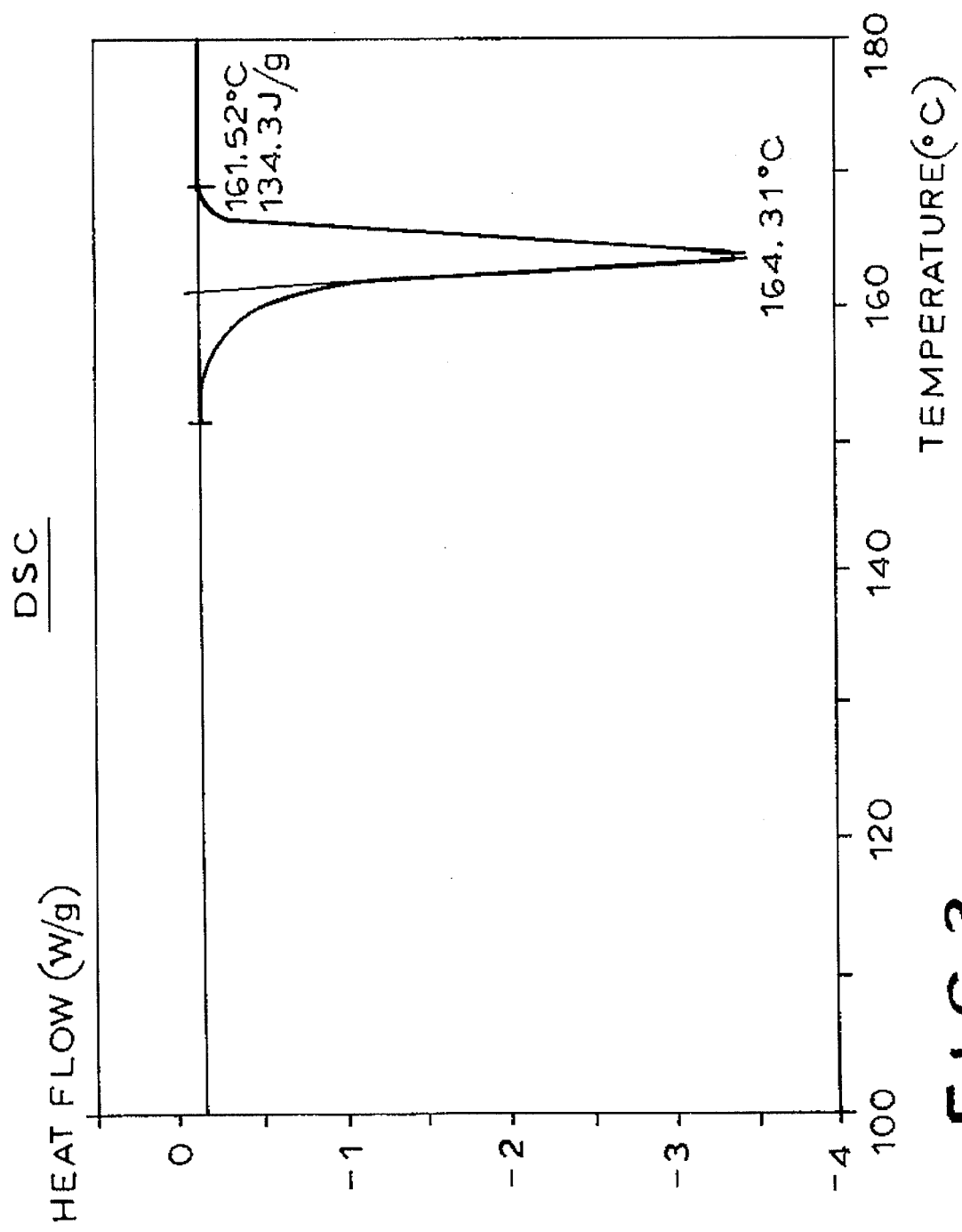
FIG. 3: DSC examination of N-(phosphonomethyl)-glycine mono-isopropylammonium salt α type crystals. Heat flow W(g against temperature °C.
Figure 6:
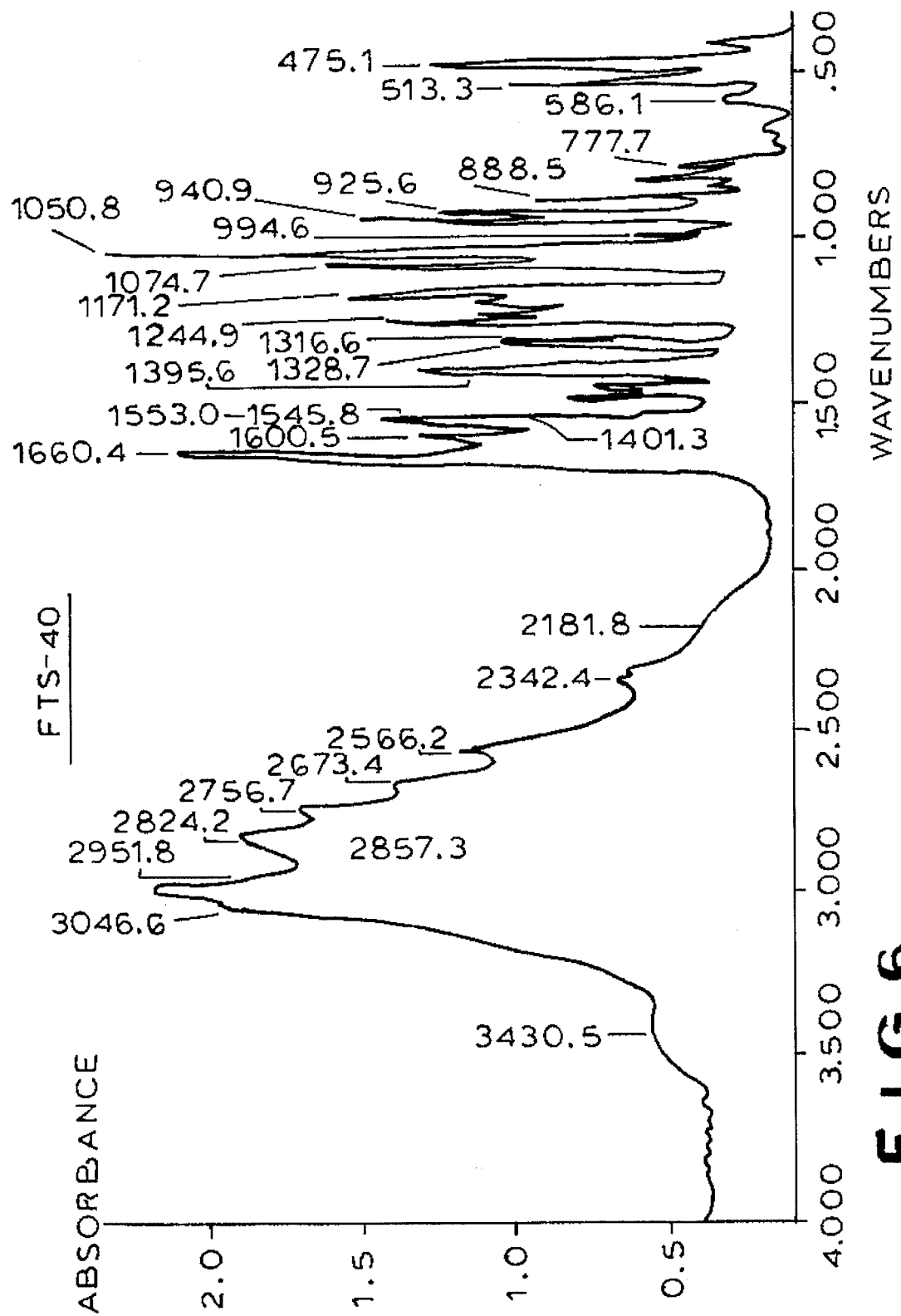
FIG. 6: IT-IR spectrum of N-(phosphonomethyl)-glycine mono-isopropylammonium salt α type crystals. Absorbance against wave numbers.

169.1 g (1mole) of 100% N-(phosphonomethyl)-glycine and 59.11 g (1 mole) of 100% pure isopropylamine are reacted in 700 ml of absolute ethanol at room temperature. The suspension is refluxed for 30 minutes, cooled to room temperature and filtered. 216.78 g (0.95 moles) of the mono-isopropylammmonium salt of N-(phosphonomethyl)-glycine are obtained. The product is crystalline, non-hygroscopic, readily soluble in water, melting at 161°–163° C. Characteristic absorption bands /FT-IR spectroscopy, cm$^{-1}$): 1660, 1600, 1553, 1545, 1075, 513, 475, characteristic values of crystal-lattice-planes measured with X-ray diffraction: 11.0, 9.06, 5.94, 5.54, 4.13, 3.71. ($\alpha$ type crystals) (FIGS. 7, 3, 6)

Example 1.13

Figure 2:
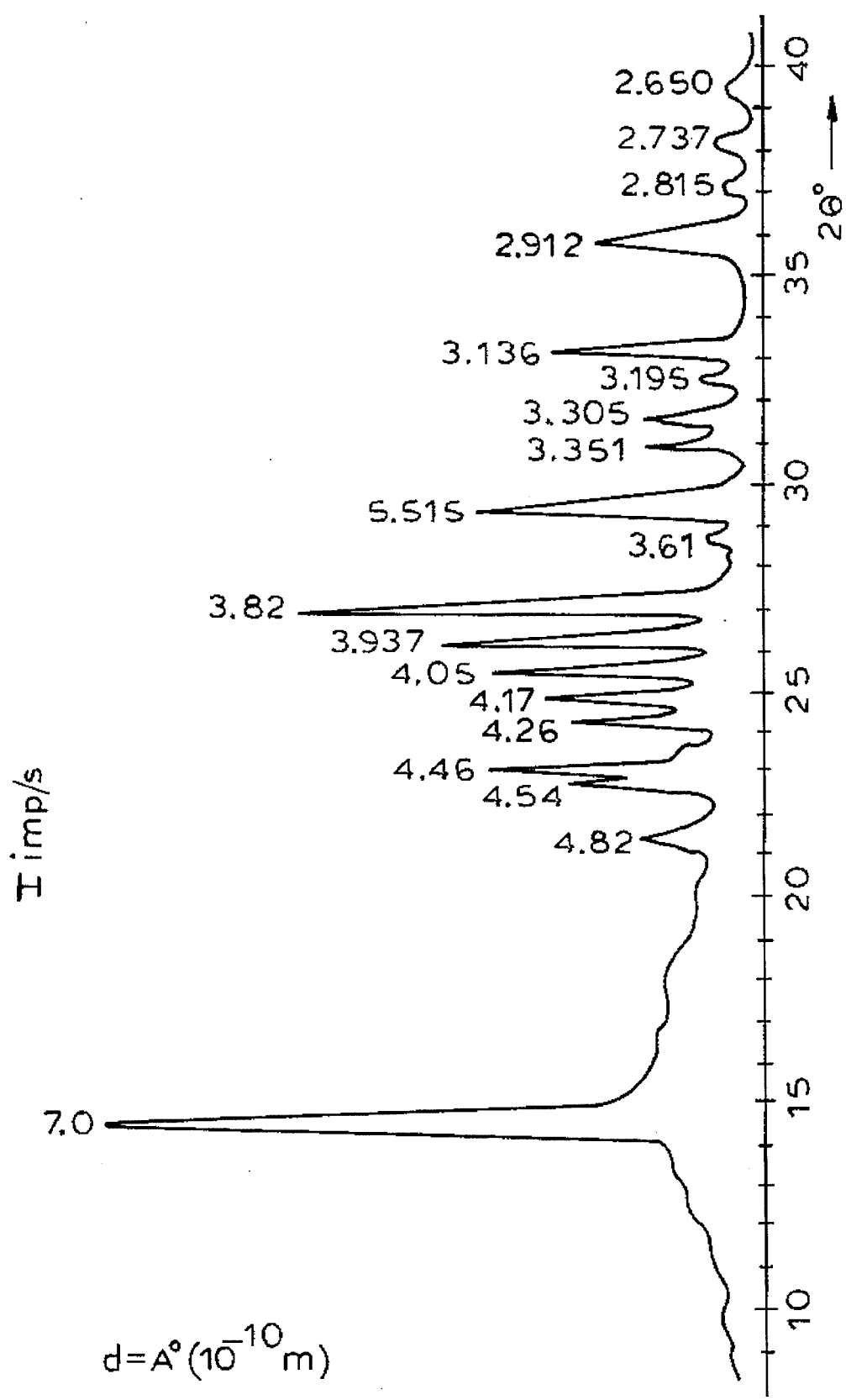
FIG. 2: X-ray diffraction spectrum of N-(phosphonomethyl)-glycine mono-isopropylammonium salt β crystal type. Intensity against angle.
Figure 4:
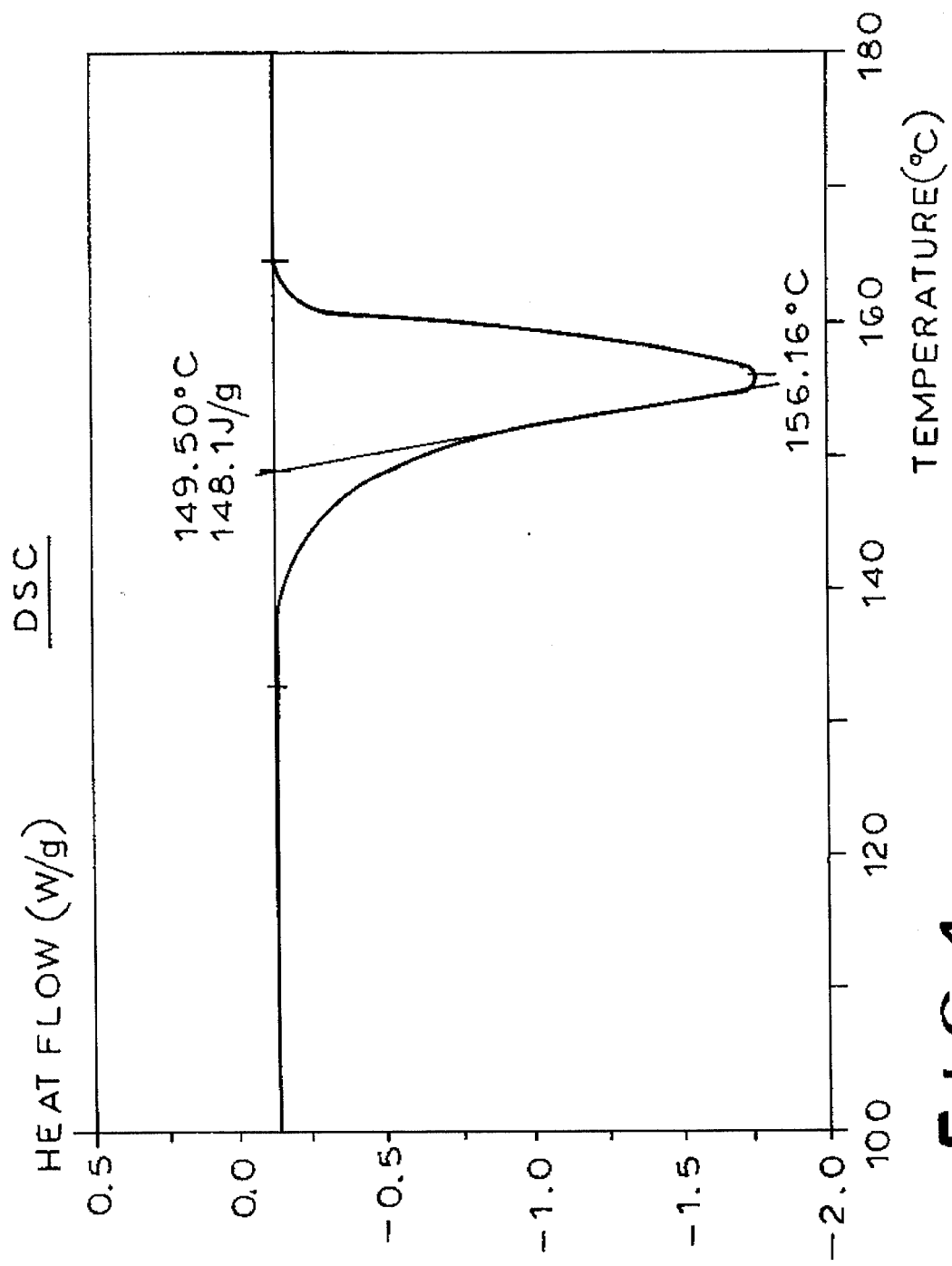
FIG. 4: DSC examination of N-(phosphonomethyl)-glycine mono-isopropylammonium salt β type crystals. Heat flow W(g against temperature °C.

The reactants as in Example 1.12 are reacted in 70 ml of distilled water, while the isopropylamine is added slowly. The solution obtained is heated for 1 hour at 100° C., cooled to room temperature, the crystals filtered and dried. 228.20 g (1 mole) of the mono-isopropylammmonium salt of N-(phosphonomethyl)-glycine are obtained. The product is non-hygroscopic, readily soluble in water, melting range 147°–153° C. (β type crystals). (FIGS. 2, 4)

Example I.14

The product obtained according to Example 1.12 is refluxed for 2×0.5 hours in 700 ml of absolute ethanol while heating, cooled at room temperature, filtered and dried. 220 g of mono-isopropylammonium salt of N-(phosphonomethyl)-glycine are obtained. The product is non-hygroscopic, readily soluble in water, melting range 148°–154° C. (β type crystals)

Example I15

16.9 g (0.1 mole) of N-(phosphonomethyl)-glycine are stirred in 40 ml of water-free ethanol and 11.9 g (0.1 mole) of isopropylamine acetate are added, followed by heating to 80° C. for 30 minutes. On cooling to room temperature the crystals are filtered, washed with ethanol and dried. The crystalline mono-isopropylammonium salt of N-(phosphonomethyl)-glycine is non-hygroscopic, readily soluble in water, melting range 154°–157° C. (β type crystals). Yield 96.6%. It contains 73.8% of N-(phosphonomethyl)-glycine.

Example I.16

The process of Example I.15 is repeated with the difference, that 14.87 g (0.125 moles) of isopropylamine acetate are used. 21.6 g of crystalline mono-isopropylammonium salt of N-(phosphonomethyl)-glycine are obtained. The product is non-hygroscopic, readily soluble in water, melting range 153°–157° C. (β type). Yield 95%. It contains 74.1% of N-(phosphonomethyl)-glycine.

Example I.17

16.9 g of N-(phosphonomethyl)-glycine are stirred in 20 ml of water and 11.9 g of isopropylamine acetate are added. The solution is clear after a while and is then poured on a watchglass. After evaporation of the water at room temperature while standing 22.8 g of crystalline mono-isopropylammonium salt of N-(phosphonomethyl)-glycine are obtained. The product is non-hygroscopic, readily soluble in water, melting range 148°–156° C. (β type). It contains 74.1% of N-(phosphonomethyl)-glycine.

Example I.18

16.9 g of N-(phosphonomethyl)-glycine are stirred in 30 ml of methanol and 9.1 g of dimethylamine-formiate are added. On working up as in the above examples 21.31 g of crystalline mono-(dimethyl-ammonium)-salt of N-(phosphonomethyl)-glycine are obtained. The product is non-hygroscopic, readily soluble in water, melting range 118°–124° C. It contains 78.3% of N-(phosphonomethyl)-glycine.

Example I.19

16.9 g of N-(phosphonomethyl)-glycine are reacted as in Example I.18 with 11.9 g of ethylamine-propionate in 30 ml of isopropanol. 19.9 g of crystalline mono-ethylammonium salt of N-(phosphonomethyl)-glycine are obtained. The product is non-hygroscopic, readily soluble in water, melting range 131°–137° C. Yield 93.1%. It contains 77.9% of N-(phosphonomethyl)-glycine.

Example I.20

360 g (2.13 moles) of N-(phosphonomethyl)-glycine are reacted at room temperature with 126 (2.13 moles) of isopropylamine in 100 ml of water. On keeping the mixture obtained below 100° C. for 1 hour it is cooled back to room temperature and after standing for 2 hours the precipitate is filtered off. The product is hygroscopic. It is extracted twice by treatment with 200 ml of absolute ethanol each, filtered and dried. 476.0 g of the mono-isopropylammonium salt of N-(phosphonomethyl)-glycine are obtained. Melting range 150°–154° C., readily soluble in water, non-hygroscopic, Yield: 98%. Contains 74% N-(phosphonomethyl)-glycine.

Example I.21

The reaction is carried out as in Example 1.20 with the difference, that the water is eliminated by evaporation and the remaining solid, hygroscopic salt is treated as indicated above.

485.6 g of the mono-isopropylammonium salt of N-(phosphonomethyl)-glycine are obtained. Melting range 150°–155° C., readily soluble in water, non-hygroscopic, Yield: 99.9%. Contains 73.8% N-(phosphonomethyl)-glycine.

Example I.22

The reaction is carried out as in Example 1.20 with the difference, that the aqueous solution obtained is dried by evaporation and the remaining solid, hygroscopic salt is treated as indicated above. The mono-isopropylammonium salt of N-(phosphonomethyl)-glycine obtained shows the melting range 148°–152° C., readily soluble in water, non-hygroscopic. Yield: 99%. Contains 73.9% N-(phosphonomethyl)-glycine.

Example I.23

360 g (2.13 moles) of N-(phosphonomethyl)-glycine are reacted with 252 g of isopropylamine (4.3 moles) at room temperature in 100 ml of water. 360 g of N-(phosphonomethyl)-glycine are added and the reaction mixture is heated below 100° C. for 1 hour. On cooling the precipitate is filtered. The hygroscopic product is extracted twice by treatment with 200 ml of absolute ethanol each, filtered and dried. 962 g of mono-isopropylammonium salt of N-(phosphonomethyl)-glycine are obtained. Melting range 154°–157° C., readily soluble in water, non-hygroscopic. Yield99%. Contains 74% N-(phosphonomethyl)-glycine.

Example I.24

360 g of N-(phosphonomethyl)-glycine are reacted with 126 g of isopropyl amine at room temperature in 100 ml of water: After precipitating the product by addition of 500 ml of absolute ethanol, the precipitate is dried and ground to give 480 g of the mono-isopropylammonium salt of N-(phosphonomethyl)-glycine. Melting range 148°–152° C., readily soluble in water, non-hygroscopic, Yield:99%. Contains 73.9% N-(phosphonomethyl)-glycine.

Example I.25

After performing the reaction as in Example I.24 and heating the aqueous reaction mixture at 100° C. for 1 hour an oily mixture is obtained which is dried in an exsiccator containing phosphorus pentoxide or calcium chloride at room temperature for 24 hours. Thereafter it is extracted with 96% ethanol, filtered and dried to give 242.5 g of the mono-isopropylammonium salt of N-(phosphonomethyl)-glycine Melting range 154°–157° C., readily soluble in water, non-hygroscopic, Yield: 99%. Contains 74% N-(phosphonomethyl)glycine.

Example I.26.

The reaction is carried out as described in Example I.25. To the oily reaction mixture obtained, 2 g of the di-isopropylammonium salt of N-(phosphonomethyl)-glycine are added which causes to precipitation of the mono-isopropylammonium salt of N-(phosphonomethyl)-glycine after stirring for 10 minutes. The white salt is filtered, extracted with . . . ml of . . . ethanol at room temperature, filtered and dried. 480 g of mono-isopropylammonium salt of N-(phosphonomethyl)-glycine are obtained. Melting range 147°–152° C., readily soluble in water, non-hygroscopic, Yield: 99%. Contains 73.6 g of N-(phosphonomethyl)-glycine.

II. FORMULATIONS

Example II.1.

A mixture of 0.5 g of ethoxylated nonyl-phenol and 2.84 of ethoxylated alkylamine additive material are dissolved in 40 ml of ethanol at room temperature. The solution is homogenized after addition of the mono-isopropylammonium salt of N-(phosphonomethyl)-glycine prepared according to Example I.2 and the ethanol is evaporated. 63.3 g of a product is obtained, which contains 69.6% g of N-(phosphonomethyl)-glycine and is non-hygroscopic, readily soluble in water.

Example II.2

A slurry in 30 ml of ethanol is prepared from the auxiliary materials comprising 1.1 g of ethoxylated nonyl-phenol, 6.39 g of ethoxylated alkyl amine, 12.69 g of ethoxylated fatty amine and 9.28 g of fatty alcohol polyglycol ether, 60 g of the mono-isopropylammonium salt of N-(phosphonomethyl)-glycine prepared according to Example I.3 are added and the slurry is homogenized after addition of 4.4 g of urea. On evaporation of the ethanol 93 g of a product are obtained, containing 47.4% of N-(phosphonomethyl)-glycine, non-hygroscopic and readily soluble in water.

Example II.3.

A slurry in 30 ml of methanol is prepared from the auxiliary materials comprising 1.53 g of ethoxylated nonyl-phenol, 3.89 g of ethoxylated alkyl amine, 7.92 g of ethoxylated fatty amine and 5.97 g of iso-tridecanol polyglycol ether, 60 g of mono-isopropylammonium salt of N-(phosphonomethyl)-glycine prepared according to Example 1.1 are added and the slurry is homogenized after addition of a mixture consisting of 2.78 g of potassium chloride, 0.03 g of 1-naphthyl acetic acid and 0.08 g of boric acid. On evaporation of the alcohol 82 g of a product are obtained, containing 53.8% of N-(phosphonomethyl)-glycine, non-hygroscopic and readily soluble in water.

Example II.4

85 g of N-(phosphonomethyl)-glycine mono-isopropylammonium salt prepared according to Example 1.2 are homogenized with a solution of 40 g of auxiliary material Hyspray in 60 ml of ethanol. On evaporation of the alcohol 125 g of a product are obtained which is non-hygroscopic, readily soluble in water and contains 50.4 g of N-(phosphonomethyl)-glycine.

Example II.5

Using the method of Example 1.11. with the difference that 10 g of lauropal-x auxiliary product are added to the slurry in surplus. A similar product as in Example 11 is obtained with the same yield.

Example II.6

Using the method of Example 1.12. with the difference that also 50 g of ammonium hydrogen carbonate are added to the slurry, and 50 g of Hyspray are used instead of 30 g. 195 g of a product are obtained which is non-hygroscopic, readily soluble in water, containing 32.3% of N-(phosphonomethyl)-glycine.

Example II.7

Using the method of Example II.4. with the difference that 80 g of Hyspray and 10 g of lauropal-x are used in 100 ml ethanol with 85 of the mono-isopropylammonium salt of N-(phosphonomethyl)-glycine prepared according to Example I.2, while 70 g of ammonium hydrogen carbonate and 50 g of ammonium sulphate are added to the slurry.

295 g of a product are obtained which is non-hygroscopic, readily soluble in water, containing 21.3% of N-(phosphonomethyl)-glycine.

Example II.8.

Using the method of Example II.7. with the difference that the quantity of Hyspray auxiliary product is 50 g, 100 ml ofethanol, 50 g of ammonium hydrogen carbonate and 500 g of ammonium sulphate used. 695 g of a product are obtained which is non-hygroscopic, readily soluble in water, containing 9% of N-(phosphonomethyl)-glycine.

Example II.9.

The auxiliary products 0.2 g of ethoxylated nonyl-phenol and 1.2 g of ethoxylated alkylamine are dissolved in 10 ml of ethanol at room temperature. The solution is homogenized with 24 g (0.1 mole) of mono-isopropylammonium-salt of (3 -amino-3-carboxy-propyl)-methane-phosphinic acid, the ethanol is evaporated. 25.3 g of a non-hygroscopic product are obtained, which is readily soluble in water containing 71% of the mono-isopropylammonium salt of (3-amino-3-carboxy-propyl)-methane-phosphinic acid.

Example II.10.

The auxiliary products 0.2 g of ethoxylated nonyl-phenol and 7.3 g of ethoxylated fatty acid are admixed with 5 ml of ethanol to give a slurry which is homogenized with 24 g (0.1 mole) of the mono-isopropylammoniumsalt of (3-amino-3 -carboxy-propyl)-methane-phosphinic acid (prepared according to Example 17, and the ethanol is evaporated. 31.4 g of a non-hygroscopic product are obtained, which is readily soluble in water and contains 57.6% of the mono-isopropylammonium salt of (3-amino-3-carboxy-propyl)-methane-phosphinic acid.

Example II.11

0.2 g of ethoxylated nonyl-phenol and 1,2 g of ethoxylated alkyl amine are admixed with 8 ml of ethanol to give a slurry which is homogenized with 19.6 g (0.1 mole) of the ammonium salt of (3-amino-3-carboxy-propyl)-methane-phosphinic acid (prepared according to Example II.8 and the alcohol is evaporated. 21.1 g of a non-hygroscopic product are obtained, which is readily soluble in water and contains 85% of the ammonium salt of (3-amino-3-carboxy-propyl)-methane-phosphinic acid.

Example II.12

0.2 g of ethoxylated nonyl-phenol, 1.2 g of ethoxylated alkyl amine and 6 g of ethoxylated fatty amine are admixed with 8 ml of ethanol to give a slurry which is homogenized with 20 g (0.1 mole) of the ammonium salt of (3-amino-3-carboxy-propyl)-methane-phosphinic acid (prepared according to Example I.11). On working as above 26.1 g of a similar product as above are obtained, containing 65% of (3-amino-3-carboxy-propyl)-methane-phosphinic acid—which in the following is abbreviated "acmpa".

Using the above methods the following compositions are prepared:

If desired the water-soluble and wettable or disperible solid products may be subjected to fine grinding in a mill or other suitable grinding means.

| Example | acmpa-salt | acmpa-content % | ethox. nonyl-phenol | ethox. fatty amine | amm. sul-fate | poly-alkox. fatty alcohol |
|---|---|---|---|---|---|---|
| II.13 | isopropyl | 98 | 2 | | | |
| II.14 | isopropyl | 84 | 1 | 15 | | |
| II.15 | ammonium | 98 | 2 | | | |
| II.16 | ammonium | 80 | 2 | 18 | | |
| II.17 | isopropyl | 84 | 1 | 10 | 5 | |
| II.18 | ammonium | 68 | 1 | 10 | 20 | 1 |

Example II.19

| | |
|---|---|
| (3-amino-3-carboxy-propyl)-methane-phosphinic acid isopropylamine salt | 33% |
| N-(phosphonomethyl)-glycine isopropylamine salt | 65% |
| ethoxylated nonylphenol | 1% |
| polyalkoxylated fatty alcohol | 1% |

Example II.20

| | |
|---|---|
| (3-amino-3-carboxy-propyl)-methane-phosphinic acid ammonium salt | 33% |
| N-(phosponomethyl)-glycine ammonium salt | 65% |
| ethoxylated nonylphenol | 1% |
| polyalkoxylated fatty alcohol | 1% |

Example II.21

| | |
|---|---|
| (3-amino-3-carboxy-propyl)-methane-phosphinic acid isopropylamine salt | 26% |
| N-(phosphonomethyl)-glycine isopropylamine salt | 53% |
| ethoxylated nonylphenol | 1% |
| ammonium sulfate | 20% |

Example II.22

| | |
|---|---|
| (3-amino-3-carboxy-propyl)-methane-phosphinic acid ammonium salt | 26% |
| N-(phosphonomethyl)-glycine ammonium salt | 53% |
| ethoxylated nonylphenol | 1% |
| ammonium sulfate | 20% |

Example II.23

| | |
|---|---|
| (3-amino-3-carboxy-propyl)-methane-phosphinic acid isopropylamine salt | 55% |
| ethoxylated fatty amine | 18% |
| imazapryl-isopropylamine | 27% |

Example II.24

| | |
|---|---|
| (3-amino-3-carboxy-propyl)-methane-phosphinic acid ammonium salt | 55% |
| ethoxylated alkyl phenol | 27% |
| imazapryl-ammonium | 27% |

Example II.25

| | |
|---|---|
| (3-amino-3-carboxy-propyl)-methane-phosphinic acid ammonium salt | 54% |
| ethoxylated fatty amine | 19% |
| imazapryl-ammonium | 27% |

Example II.26

| | |
|---|---|
| (3-amino-3-carboxy-propyl)-methane-phosphinic acid isopropylamine salt | 32% |
| ethoxylated alkyl amine | 4% |
| 2,2-D-isopropylamine salt? | 64% |
| ethoxylated nonyl phenol | 1% |

Example II.27

| | |
|---|---|
| (3-amino-3-carboxy-propyl)-methane-phosphinic acid isopropylamine salt | 30% |
| polyalkoxylated fatty alcohol | 20% |
| Triazine | 30% |
| silicon dioxide | 5% |
| ammonium sulphate | 15% |

Example II.28

| | |
|---|---|
| (3-amino-3-carboxy-propyl)-methane-phosphinic acid ammonium salt | 30% |
| polyoxylated fatty alcohol | 15% |
| Triazine | 30% |
| ammonium sulphate | 25% |

Example II.29

| | |
|---|---|
| (3-amino-3-carboxy-propyl)-methane-phosphinic ammonium salt | 68& |
| Oxyfluorophen | 14% |
| ethoxylated nonyl-phenol | 1% |

Example II.30

1 kg of the compositions prepared according to the Examples above are filled into a bag the size of which is suitable to take the quantity. The bag is made of poly-(vinyl-alcohol), which is plastified with a polyvalent alcohol. The bag is square shaped and is closed on its three sides. The properties of the powders according to the examples as above are such that it is easy to fill the same into the bags. The bags are then closed by welding.

When using the above bags—after storing and transfering the same to the place of use—they are thrown into the needed amount of water while stirring intensely. The polymer disappears within 2 minutes while the herbicide composition is dissolved completely or is dispersed in the water to give a composition which can be used directly in the field.

In the following Examples different water-soluble or water-wettable solid compositions are enumerated. The active ingredient non-hygroscopic mono-isopropylammonium salt of N-(phosphonomethyl)-glycine is always abbreviated "solid glyphosate mono-ipa-salt".

Example II.31

| | |
|---|---|
| Solid glyphosate mono-ipa-salt | 98% |
| Ethoxylated nonyl-phenol | 2% |

Example II.32

| | |
|---|---|
| Solid glyphosate mono-ipa-salt | 95% |
| Ethoxylated-nonyl-phenol | 1% |
| Ethoxylated alkylamine | 4% |

Example II.33

| | |
|---|---|
| Solid glyphosate mono-ipa-salt | 80% |
| Ethoxylated-nonyl-phenol | 2% |
| Ethoxylated fatty amine | 18% |

Example II.34

| | |
|---|---|
| Solid glyphosate mono-ipa-salt | 77% |
| Ethoxylated-nonyl-phenol | 1% |
| Ethoxylated alkylamine | 7% |
| Ethoxylated fatty amine | 10% |
| Urea | 5% |

Example II.35

| | |
|---|---|
| Solid glyphosate mono-ipa-salt | 60% |
| Ethoxylated-nonyl-phenol | 1% |
| Ethoxylated alkylamine | 7% |
| Ethoxylated fatty amine | 10% |
| Polyalkoxylated fatty alcohol | 2% |
| Ammonium-sulphate | 20% |
| polyoxyethylated fatty acid | 5% |
| ammonium sulphate | 5% |
| silicon dioxide | 5% |

Example II.36

| | |
|---|---|
| Solid glyphosate mono-ipa-salt | 70% |
| Ethoxylated-nonyl-phenol | 1% |
| Ethoxylated alkylamine | 4% |
| Ammonium-sulphate | 20% |
| Silicon dioxide | 5% |

Example II.37

| | |
|---|---|
| Solid glyphosate mono-ipa-salt | 68.00% |
| Ethoxylated-nonyl-phenol | 2.00% |
| Ethoxylated-alkylamine | 4.50% |
| Ethoxylated fatty amine | 9.60% |
| Isotridecyl alcohol-polyglycolether | 7.30% |
| KCl | 3.45% |
| 1-naphthyl acetic acid | 0.05% |
| Boric acid | 0.10% |

Example II.38

| | |
|---|---|
| Solid glyphosate mono-ipa-salt | 50% |
| Isopropylammonium salt of 2,4-D | 32% |
| Ethoxylated-nonyl-phenol | 1% |
| Ethoxylated-alkylamine | 4% |
| Ammonium-sulphate | 8% |
| Silicon dioxide | 5% |

Example II.39

| | |
|---|---|
| Solid glyphosate mono-ipa-salt | 40% |
| Glufosinate mono-ipa-salt | 7% |
| Ethoxylated-nonyl-phenol | 2% |
| Sodium-lignine sulphonate | 3% |
| Ammonium-sulphate | 33% |
| Silicon dioxide | 5% |
| Caoline | 10% |

Example II.40

| | |
|---|---|
| Solid glyphosate mono-ipa-salt | 40% |
| Dimethipine | 7% |
| Ethoxylated-nonyl-phenol | 2% |
| Sodium-lignine sulphonate | 3% |
| Ammonium-sulphate | 33% |
| Silicon dioxide | 5% |
| Caoline | 10% |

Example II.41

| | |
|---|---|
| Solid glyphosate mono-ipa-salt | 50% |
| Oxyfluorphen | 4% |
| Ethoxylated-nonyl-phenol | 2% |
| Sodium-lignine sulphonate | 3% |
| Silicon dioxide | 16% |
| Caoline | 20% |

Example II.42

| | |
|---|---|
| Solid glyphosate mono-ipa-salt | 40% |
| Ethoxylated-nonyl-phenol | 1% |
| Ethoxylated alkylamine | 4% |
| Ethoxylated fatty amine | 15% |

-continued

| Ammonium-sulphate | 30% |
|---|---|
| Caoline | 10% |

Example II.43

| Solid glyphosate mono-ipa-salt | 80% |
|---|---|
| ATPLUS 411 | 19% |
| Polyalkoxylated fatty alcohol | 1% |

Example II.44

| Solid glyphosate mono-ipa-salt | 40% |
|---|---|
| Glufosinate ammonium salt | 20% |
| Ethoxylated nonyl-phenol | 1% |
| Ethoxylated alkylamine | 4% |
| Ammonium-sulphate | 35% |

Example II.45

| Solid glyphosate mono-ipa-salt | 0.05% |
|---|---|
| Ammonium-sulphate | 80.00% |
| Ethoxylated nonyl-phenol | 1.00% |
| Ethoxylated fatty amine | 18.95% |

Example II.46

| Solid glyphosate mono-ipa-salt | 99% |
|---|---|
| Ethoxylated nonyl-phenol | 1% |

Example II.47

| Solid glyphosate mono-ipa-salt | 1% |
|---|---|
| Dissovet S | 99% |

Example II.48

| Solid glyphosate mono-ipa-salt | 1% |
|---|---|
| Ammonium-sulphate | 70% |
| Ammonium-nitrate | 28% |
| Polyalkoxylated fatty alcohol | 1% |

Example II.49

| Solid glyphosate mono-ipa-salt | 99.9% |
|---|---|
| Polyalkoxylated fatty alcohol | 0.1% |

Example II.50

68 g of mono-isopropylammmonium salt of N-(phosphonomethyl)-glycine, 3 g of 3,6-dichloro-2-pyridine-2-carbonic acid, 10 g of lignine sulphonic acid potassium salt, 1 g of oleyl-methyltauric acid sodium salt, 4 g of polyoxylated nonylphenol, 4 g of polyethane-alkylamide and 10 g of synthetic silicium dioxyde are ground to 7–15 micron size. A wettable powder is obtained which contains 50% of N-(phosphonomethyl)-glycine and 17.5% of metribezine, which can be used in the known manner.

Example II.51

68 g of mono-isopropylammonium salt of N-(phosphonomethyl)-glycine, 10 g of 2,3-dihydro-5,6-dimethyl-1,4-lithium- 1,1,4,4-tetroxide, 3 g of polyethoxylated nonylphenol, 7 g of polyethoxylated fatty acid amine, 7 g of ligninesulphonic acid potassium salt and 5 g of synthetic silicon dioxide are ground to the desired size to give a non-hygroscopic product for agricultural use.

Example II.52

68 g of mono-isopropylammonium salt of N-(phosphonomethyl)-glycine, 8.75 g of 4-amino-3-methylmercapto-6-tert.butyl- 1,2,4-triazine, 5 g of lignine-sulphonic acid potassium salt, 5 g of polyethoxylated nonyl-phenol, 1 g of oleyl-methyltauric acid sodium salt and 12.25 g of Aerosil are ground to 7–15 micron size. The powder obtained is non-hygroscopic, N-(phosphonomethyl)-glycine content: 50%. It can be used for suspension formulations to be used in agriculture.

III. ANALYTICAL TESTS

III.1. FREE FLOW TESTS

When making formulations for use in the water-soluble bags according to our invention it is necessary to subject the products to the free-flow test in order to clarify whether or not they are suitable for this purpose.

100 of the non-hygroscopic salts according to the invention are filled into a funnel having a 2 cm width opening off-take and the period of time is determined which is needed for the product to flow out. For free-flowing powders or such that are considered to have good flowing properties, this has to happen within 10 seconds. Table I shows some results obtained with some products according to our invention

TABLE I

| Example | Flowing time (sec) |
|---|---|
| II.31 | 4.0 |
| II.32 | 2.0 |
| II.33 | 4.0 |
| II.34 | 2.0 |
| II.35 | 1.5 |
| II.36 | 2.0 |
| II.37 | 7.0 |
| II.38 | 5.0 |
| II.39 | 5.0 |
| II.40 | 9.5 |
| II.41 | 7.2 |
| II.42 | 4.5 |
| II.43 | 4.0 |
| II.44 | 3.0 |
| II.12 | 5.0 |
| II.13 | 5.0 |

III.2 X-RAY DIFFRACTION TESTS

The following samples of different mono-isopropylammonium salts of N-(phosphonomethyl)-glycine were subjected to examination, prepared substantially according to the Examples as indicated:

TABLE II

| Example | solvent used | crystal type found |
|---|---|---|
| I.12 | abs. ethanol | α |
| I.1 | 96% ethanol | α |
| I.13 | water | β |
| — | methanol/diethyl ether* | β |

*freshly prepared

Method: The tests were performed using an X-ray diffractometer of the HZG-4/C type. Source of irradiation: $CoK_\alpha \lambda = 1.79$ A° (Co tube 30 keV 12 mA° Fe filter). Goniometer sensor velocity 1°/minute. The sample holder was made of Al.

Figure 5:
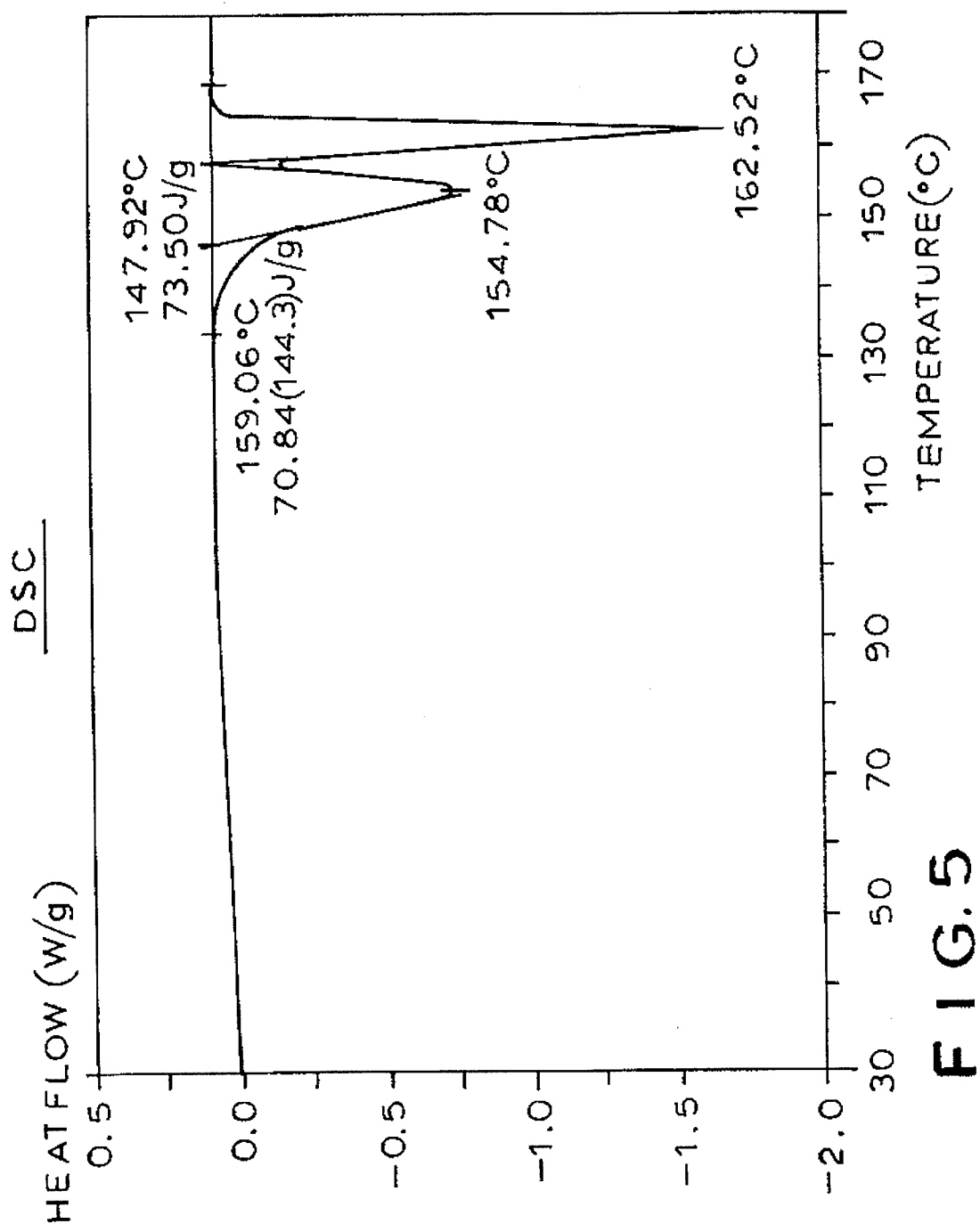
FIG. 5: DSC examination of N-(phosphonomethyl)-glycine mono-isopropylammonium salt e type and β type crystals in a mixture of 1:1. Heat flow W/g against temperature °C.

The method of preparing the samples and testing were always the same. On the basis of the X-ray-grams the d lettice level values were calculated and their relative intensities were given as indicated in Table III. Some of the X-ray-grams are also shown as FIGS. 4 and 5.

It is clear form the results that the samples show two different structures which we designated crystal types α and β respectively as indicated in Table II.

TABLE III

| abs. ethanol | | 96% ethanol | | methanol-diethyl-ether | | water | |
|---|---|---|---|---|---|---|---|
| dA° | $I/I_o$ | dA° | $I/I_o$ | dA° | $I/I_o$ | dA° | $I/I_o$ |
| 11.0 | 100 | 11.0 | 100 | 7.03 | 100 | 7.00 | 100 |
| 9.06 | 47 | 9.09 | 45 | 4.83 | 16 | 4.83 | 13 |
| 7.41 | 13 | 7.39 | 14 | 4.56 | 19 | 4.54 | 29 |
| 5.94 | 43 | 5.95 | 43 | 4.48 | 46 | 4.47 | 43 |
| 5.54 | 38 | 5.56 | 46 | 4.27 | 23 | 4.26 | 29 |
|  |  | 5.38 | 9 | 4.17 | 46 | 4.17 | 33 |
| 4.98 | 12 | 5.0 | 15 | 4.06 | 37 | 4.05 | 40 |
| 4.85 | 33 | 4.86 | 37 | 3.937 | 48 | 3.937 | 49 |
| 4.55 | 9 | 4.56 | 10 | 3.831 | 65 | 3.820 | 76 |
|  |  | 4.37 | 11 | 3.621 | 6 | 3.62 | 7 |
| 4.298 | 9 | 4.30 | 9 | 3.527 | 55 | 3.515 | 48 |
| 4.13 | 83 | 4.13 | 94 | 3.358 | 21 | 3.351 | 20 |
|  |  | 4.08 | 31 | 3.297 | 18 | 3.30 | 19 |
| 4.01 | 58 | 4.01 | 48 | 3.198 | 10 | 3.195 | 9 |
| 3.82 | 14 | 3.83 | 15 | 3.140 | 39 | 3.136 | 34 |
| 3.782 | 15 | 3.79 | 12 | 2.917 | 37 | 2.912 | 28 |
| 3.710 | 51 | 3.71 | 56 | 2.821 | 4 | 2.815 | 6 |
|  |  | 3.59 | 6 | 2.739 | 11 | 2.737 | 8 |
| 3.48 | 10 | 3.488 | 11 | 2.654 | 6 | 2.650 | 6 |
| 3.403 | 29 | 3.403 | 24 | 2.547 | 7 | 2.545 | 10 |
| 3.295 | 9 | 3.293 | 9 | 2.502 | 6 | 2.502 | 8 |
| 3.257 | 17 | 3.259 | 16 | 2.421 | 12 | 2.420 | 18 |
| 3.189 | 29 | 3.191 | 34 | 2.35 | 21 | 2.405 | 11 |
| 3.035 | 7 | 3.037 | 6 |  |  | 2.34 | 15 |
| 2.985 | 6 | 2.983 | 6 |  |  |  |  |
| 2.929 | 7 | 2.932 | 7 |  |  |  |  |
|  |  | 2.909 | 6 |  |  |  |  |
| 2.790 | 10 | 2.789 | 10 |  |  |  |  |
|  |  | 2.688 |  |  |  |  |  |
| 2.502 | 18 | 2.502 | 24 |  |  |  |  |

III.3. SOLUBILITY TESTS

III.31

Table IV illustrates some solubility values of the mono-isopropylammonium salts and di-isopropylammonium salts of N-(phosphonomethyl)-glycine on the basis of which the processes according to our invention can be reduced to practice. All solvents or solvent-mixtures can be used for our processes which show a reasonable solubility-difference between the salts and products that have to be separated.

TABLE IV

| | SOLUBILITY g/liter | | |
|---|---|---|---|
| solvent | mono-IPA* salt | di-IPA* salt | glyphosate** |
| water | 1470 | 1980 | 12 |
| methanol | 56 | 570 | <0.3 |
| ethanol |  |  | 0.2 |
| n-propanol | 0.7 | 170 | <0.5 |
| isopropanol |  |  | <0.5 |
| n-butanol | 0.1 | 35 |  |
| benzyl-alcohol | 0.5 | 420 | <0.2 |
| propylene-glycol | 184.0 | 244 | <0. |
| dimethyl-formamide | 1.8 | 22 | <0.2 |
| benzene | <0.1 | <0.1 | <0.1 |
| isopropyl amine | <0.1 | <0.1 |  |

\* = iso-propyl amine
\*\* = N-(phosphonomethyl)-glycine

Example III.32

The values given below can be used to evaluate the best solvents to be used in the case of (3-amino-3-carboxypropyl)-methane phosphinic acid.

TABLE V

| | SOLUBILITY g/liter (25° C.) | | |
|---|---|---|---|
| solvent | mono-ammonium salt | mono-ipa-salt | glufosinate |
| water | 2000 | 1150 | 99 |
| methanol | 14 | 260 | 23 |
| ethanol | 4 | 5 | 9 |
| n-propanol | 6 | 5 | 9 |
| isopropanol | 10 | 4 | 12 |
| benzylalcohol | 9 | 300 | 9 |
| propylene-glycol | 9 | 280 | 21 |
| dimethyl formamide | 10 | 8 | 12 |
| benzene | — | — | 7 |

III. UPTAKE OF HUMIDITY

III.1

The samples were investigated in open containers, at 60% humidity and 25° C. The results are shown in Table VI.

| | days | | | | | |
|---|---|---|---|---|---|---|
| salt | 1 | 2 | 7 | 14 | 30 | 90 |
| mono-isopropyl-ammonium salt of N-(phosphonomethyl)-glycine* | 0.1% | 0.1% | 0.1% | 0.1% | 0.1% | 0.1% |
| di-isopropyl-ammonium salt of N-(phosphonomethyl)-glycine** | 13.0% | 14.5% | 16.1% | 18.8% | 19.2% | 30.9% |

Appearance:
*the mono-isopropylammonium salt was unchanged after 30 days.
*the di-isopropylammonium salt was sticky and hygroscopic within 1 day and was completely liquid within 14 days.

IV. BIOLOGICAL EXAMPLES

IV.1

Compositions formulated according to Examples II.34 or II.36 are dispersed in water to give 3 g active ingredient/liter liquids. 6 mg of the active ingredient of each sample were sprayed on 15 day old barley plants, kept in vessels under green house conditions. On the 4th day the clorofil quantity falling on unit quantities of dry substance in the plants was determined. The results are shown in Table VII

TABLE VII

| Control | 9.26 mg/g |
|---|---|
| Example II.9 | 3.42 mg/g |
| Example II.11 | 3.43 mg/g |

Growth depression was determined as well. The results are shown in Table VIII.

TABLE VIII

| Control | 0 |
|---|---|
| Example II.9 | 8.75 cm |
| Example II.11 | 8.5 cm |

IV.2

According to the methods of Example V.1. 15 day old bean plants were sprayed with 4.5 mg of active ingredient/vessel (1.5 ml of the liquid) and the photosynthetic activity was determined on the third day. The result are summarized on Table IX.

TABLE IX

|   | Control | Example II.9 | Example II.11 |
|---|---|---|---|
| F | 685 | 340 | 325 |
| F | 556 | 89 | 116 |
|   | 0.517 | 0.062 | 0.134 |
|   | 2.402 | 0.404 | 0.929 |

We claim:

1. A solid, non-hygroscopic salt of the Formula (I)

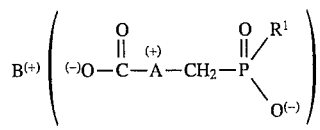

wherein $R^1$ is hydroxy or alkyl;

A is $C_1$ to $C_4$ alkyl-amino or an amino-alkyl group containing a primary or a secondary amino group; and B is ammonium ion or an alkyl-substituted ammonium ion, which is substantially free of a diammonium salt of the Formula (V):

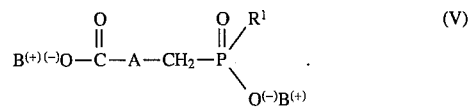

2. A solid, non-hygroscopic mono-isopropylammonium salt of N-(phosphonomethyl)-glycine according to claim 1 of the α crystal type, having a melting point range of 158°–163° C. and the characteristic values of crystal-lattice-levels when measured by way of X-ray-diffraction are as follows: 11.0, 9.06, 5.94, 5.54, 4.13, 3.71 A, while the characteristic absorption bands obtained by FT-IR-spectroscopy are 1660, 1600, 1553, 1545, 1075, 513 and 475 $cm^{-1}$.

3. A solid, non-hygroscopic crystalline mono-isopropylammonium salts of N-(phosphonomethyl)-glycine according to claim 1 of the β crystal type, having a melting range of 143°–157° C. and the characteristic values of crystal-lattice-levels when measured by way of X-ray-diffraction are as follows: 7.00, 4.83, 4.47, 3.35, 2.815 A°, while the characteristic absorption bands obtained by FT-IR-spectroscopy are 1645, 1594, 1561, 1541, 1066, 500 and 455 $cm^{-1}$.

4. A solid, non-hygroscopic crystalline (3-amino-3-carboxypropyl)-methane-phosphinic acid mono-isopropylammonium salt according to claim 1, having a melting range of 199°–203° C., while the characteristic absorption bands obtained by FT-IR-spectroscopy are 1640, 1601, 1530, 1138, 1037, 750 and 471 $cm^{-1}$.

5. The solid, non-hygroscopic salt of the Formula (I) defined in claim 1 substantially free of a surfactant.

* * * * *